(12) United States Patent
Deinzer et al.

(10) Patent No.: US 8,244,331 B2
(45) Date of Patent: Aug. 14, 2012

(54) METHOD AND DEVICE FOR DETERMINING AN OPTIMUM DIRECTION OF PROJECTION FOR RECORDING PROJECTION IMAGES

(75) Inventors: Frank Deinzer, Röthenbach (DE);
Esther-Sabrina Platzer, Jena (DE);
Matthias Wacker, Jena (DE)

(73) Assignee: Siemens Aktiengesellschaft, München (DE)

( * ) Notice: Subject to any disclaimer, the term of this patent is extended or adjusted under 35 U.S.C. 154(b) by 1023 days.

(21) Appl. No.: 12/229,754

(22) Filed: Aug. 26, 2008

(65) Prior Publication Data
US 2009/0082990 A1 Mar. 26, 2009

Related U.S. Application Data

(60) Provisional application No. 60/969,199, filed on Aug. 31, 2007.

(51) Int. Cl.
*A61B 6/00* (2006.01)
(52) U.S. Cl. ............ 600/431; 600/425; 382/130; 378/4; 378/21; 378/901; 702/19; 702/150; 424/9.4
(58) Field of Classification Search .................. 600/407, 600/410, 419, 420, 425, 431; 382/128, 130; 378/4, 8, 21, 901; 702/19, 150; 424/9.4
See application file for complete search history.

(56) References Cited

U.S. PATENT DOCUMENTS

| | | | |
|---|---|---|---|
| 6,230,040 B1* | 5/2001 | Wang et al. | 600/415 |
| 6,574,297 B2* | 6/2003 | Tam | 378/15 |
| 7,522,744 B2* | 4/2009 | Bai et al. | 382/100 |
| 7,831,097 B2* | 11/2010 | Chen et al. | 382/207 |
| 2006/0153468 A1* | 7/2006 | Solf et al. | 382/254 |
| 2008/0171936 A1* | 7/2008 | Homan et al. | 600/424 |

FOREIGN PATENT DOCUMENTS

| | | |
|---|---|---|
| DE | 102007015306 A1 | 10/2008 |
| DE | 102007024451 A1 | 12/2008 |

OTHER PUBLICATIONS

J Henning, K Scheffler, J Laubenberger, R Strecker. Time-Resolved Projection Angiography after Bolus Injection of Contrast Agent. Magnetic Resonance in Medicine, 37:341-345 (1997).*

(Continued)

*Primary Examiner* — Brian Casler
*Assistant Examiner* — Amanda Lauritzen

(57) ABSTRACT

The invention relates to a method and a device for determination of an optimum direction of projection or position for recording a number of two-dimensional projection images of an object of interest, with the two-dimensional projection images being recorded by rotation or translation of an imaging system around the object. Inventively the process is as follows: a) estimating a position of the object at a point in time; b) determining at least one optimum imaging view from which the optimum direction of projection and/or position is produced, for the position estimated under a) with the aid of previously determined measurement. Preferably the measurement is expressed as a function of a transformation which is described by a spatial object-imaging system relationship.

18 Claims, 3 Drawing Sheets

OTHER PUBLICATIONS

Esther-Sabrina Platzer; "Visualisierung von Blutfluss im 3-D aus 2-D-Angiogrammen"; Platzer; Diplomarbeit, Universität Koblenz-Landau and Siemens Medical Solutions Forchheim, Aug. 2006; pp. i-x and 1-179. Aug. 2006; [retrieved online] http://www.uni-koblenz.de/FB4/Publications/Theses/ShowThesis?id=1893#ref1vorr. nicht veröfientlicht.

H. Schmitt, M. Grass, V. Rasche, O. Schramm, S. Haehnel, K. Sartor; "An X-Ray-Based Method for the Determination of the Contrast Agent Propagation in 3-D Vessel Structures"; IEEE Transactions on Medical Imaging, vol. 21, No. 3, Mar. 2002; pp. 251-262.

H. Schmitt, Michael Grass, Rolf Suurmond, Thomas Köhler, Volker Rasche, Stefan Hähnel, Sabine Heiland; "Reconstruction of blood propagation in three-dimensional rotational X-ray angiography (3D-RA)"; Computerized Medical Imaging and Graphics, Oct. 2005; vol. 29 No. 7, pp. 507-520, Epub Sep. 2, 2005.

Svetla Petkova, Alamgir Hossain, Jamal Naser, Enzo Palambo; "CFD Modelling of blood flow in portal vein hypertension with and without thrombosis"; Third International Conference on CFD in the Minerals and Process Industries, CSIRO, Melbourne, Australia, Dec. 10-12, 2003. http://www.cfd.com.au/cfd_conf03/papers/133Hos.pdf; Melbourne, Australia.

* cited by examiner

METHOD AND DEVICE FOR DETERMINING AN OPTIMUM DIRECTION OF PROJECTION FOR RECORDING PROJECTION IMAGES

CROSS REFERENCE TO RELATED APPLICATIONS

The present application claims the benefit of a provisional patent application filed on Aug. 31, 2007, and assigned application No. 60/969,199, which is incorporated by reference herein in its entirety.

FIELD OF THE INVENTION

The invention relates to a method and a device for determining at least one optimum direction of projection and/or position for recording a number of two-dimensional projection images of an object, with the two-dimensional projection images being recorded by rotation and/or translation of an imaging system around the object.

BACKGROUND OF THE INVENTION

In clinical practice the diagnosis of vascular diseases such as aneurysms or stenoses is for example essentially based on chronological two-dimensional angiography sequences (in which the blood flow is to be seen). In these examination methods a contrast medium is injected into the bloodstream of a vessel and a sequence of x-ray images is recorded in order to record its propagation over time (bolus front). In addition static three-dimensional volume datasets can be used for diagnosis, which as a rule show a completely filled vessel tree.

Whereas aneurysms mostly show up very clearly in the corresponding images, stenoses are as a rule relatively hard to see. Instead the angiograph shows points in the vessel at which a greatly reduced blood flow is occurring. If a stenosis leads to a complete closure of a vessel the result is that the corresponding vessel, as well as all further vessels supplied by said vessel, are no longer detectable in the x-ray image.

Since the images arising are merely projections of the volume observed, with unfavorable directions of projection overlaying of the vessels occurs in the two-dimensional projections which leads to information loss. In a three-dimensional reconstruction of the blood flow from a 2D angiography sequence this leads to problems since ambiguities can occur during back projection. FIG. 1 gives an example to illustrate this problem of ambiguities. FIG. 1 shows a view A, in which there is back projection from a 2D projection 2D into a 3D volume 3D. A Pixel P is no longer able to be assigned uniquely to a voxel (a number of adjacent voxels lying behind one another) but under some circumstances can be mapped onto a number of voxels V1, V2 belonging to different vessel sections. Even in the 2D projection this demands precise observation to assign of the flow of contrast medium to a vessel. Expressed in general terms the loss of information of the depth information which is caused by the projection makes diagnosis of possible diseases difficult or even makes it impossible to detect said diseases.

To avoid vessel overlays in the 2D projections test fluoroscopy images are prepared at the beginning of each angiography sequence. On the basis of these the doctor maneuvers the detector manually to a suitable position. Subsequently a test image is created again to check the positioning. This process is repeated until such time as an optimum possible view of the entire vessel tree has been found. This means a significantly greater exposure to radiation for the patient than is necessary for the actual angiography sequence. In addition manual alignment is time-intensive since several attempts are needed to establish a suitable patient-detector alignment.

Biplanar angiography systems are a further alternative, in which two views offset by 90° are created for each fluoroscopy step. For very simple vessel overlaying this is a way of reducing ambiguities. For complex vessel structures, even the use of such systems does not allow overlapping of vessels in the projections to be completely avoided.

There are different approaches to dealing with the ambiguities which arise in conjunction with a 3-dimensional blood flow reconstruction. Methods such as those described in [1] and [2] solve the problem with heuristic assumptions and the exclusion of the ambiguous information. In [3], [4] and [5] an approach is already known or has been proposed with which, for each of the ambiguities arising, the probability can be computed of the hypothesis made by the back projection involving correct information or incorrect information.

Basically ambiguities can be reduced by selecting a favorable camera position. Since the bolus front moves however, the determination of a good fixed camera position for the entire sequence of recorded images is possible but a single angle of observation cannot supply optimum information with complicated vessel systems.

SUMMARY OF THE INVENTION

The object of the invention consists of designing a method or a device of the type mentioned at the start so that the possible ambiguities mentioned above are reduced in the zone of interest at a relevant point in time.

This object is achieved by the features of the independent claims. Advantageous developments of the invention are specified in the dependent claims.

Different camera positions or recording views at different points in time can provide a greater degree of information for the zone of interest of the bolus front.

Using a 3D vessel tree as its starting point, which can be provided by 3D angiography, the inventive process is as follows:

a) Estimating a position (A1, A2) of the object at a point in time,
b) Determination of at least one optimum imaging view, from which the optimum direction of projection and/or position is produced, for the position estimated under a) with the aid of a measurement determined beforehand.

In such cases the object preferably represents the position of a bolus front in the body of a patient.

Steps a) and/or b) can be repeated in such cases.

In order to approximate the zone or interest for which an optimum view is to be found, the bolus front must be estimated in the 3D volume as a function of time. To this end the blood flow is first simulated with the aid of simulation methods, for example from computational fluid dynamics, in the individual vessel volume. The fundamentals of this process are described in [2].

Within the framework of the simulation, based on physical laws, the flow movement through the vessels is computed. Navier-Stokes equations, which make a numerical approximation of so-called reactive flows possible, form the basis for the simulation. The Navier-Stokes equations form a complex of differential equations which represent the laws of physics. Essentially they are based on the conservation equations for mass, impulse, energy and if necessary also rotational impulse. In the simulation the viscosity and the density of the blood as well as effects of external pressure on the vessel are taken into account. By using the Navier-Stokes equations on a specific vessel system—with sufficiently accurate computation and sufficient information about the vessel system and the other ambient conditions—a physically correct simulation of the blood flow is made possible.

In order subsequently to be able to determine an optimum position and alignment sequence the term optimality and an associated measurement for it is to be defined which can be compared for different positions if necessary at different points in time.

The measurement is expressed as a function of a transformation (position and orientation) under which the volume of the object is observed. For this the volume is projected perspectively onto a plane of projection or onto a detector plane (this implies the observation of the detector plane as a two-dimensional plane in the three-dimensional including a perspective center, which in reality corresponds to the x-ray source).

In this case the measure is expediently expressed as a function of a transformation which is described by a spatial relationship between object and imaging system, with a superlinear function, especially a squaring, being applied on the line integrals along the projection rays in the direction of projection and its results summed.

In an advantageous manner the measurement can be provided with a weighting mask. The measurements at different points in time can be compared with each other and/or their minimum determined. Expressed in other words, the minimum expediently corresponds to the minimum of an optimum recording view.

In accordance with an advantageous further development of the invention transformations determined can be converted to the coordinate system of the recording system.

A further aspect of the invention is a medical device, especially an examination and/or treatment device, embodied to execute said inventive method.

The invention has the following advantages:
Since there are no initial test images for determining a camera setting and the use of biplanar angiography systems can be dispensed with, the exposure to radiation for the patient is significantly reduced; multiple fluoroscopy for positioning is omitted.
The omission of the alignment phase which has to be repeatedly assessed visually means that the inventive method saves time.
The level of ambiguities is reduced. The quality of the information obtained thus increases.
The sequence of suitable positions arising is suited in connection with the transformation information as input for back projection methods which visualize the blood flow in 3D and/or use sequences to support its simulation. (see e.g. [4] and [5])

BRIEF DESCRIPTION OF THE DRAWINGS

Advantageous embodiments of the invention are given in greater detail below based on an exemplary embodiment which refers to a drawing.

The drawing shows the following.

DETAILED DESCRIPTION OF THE INVENTION

Figure 1:
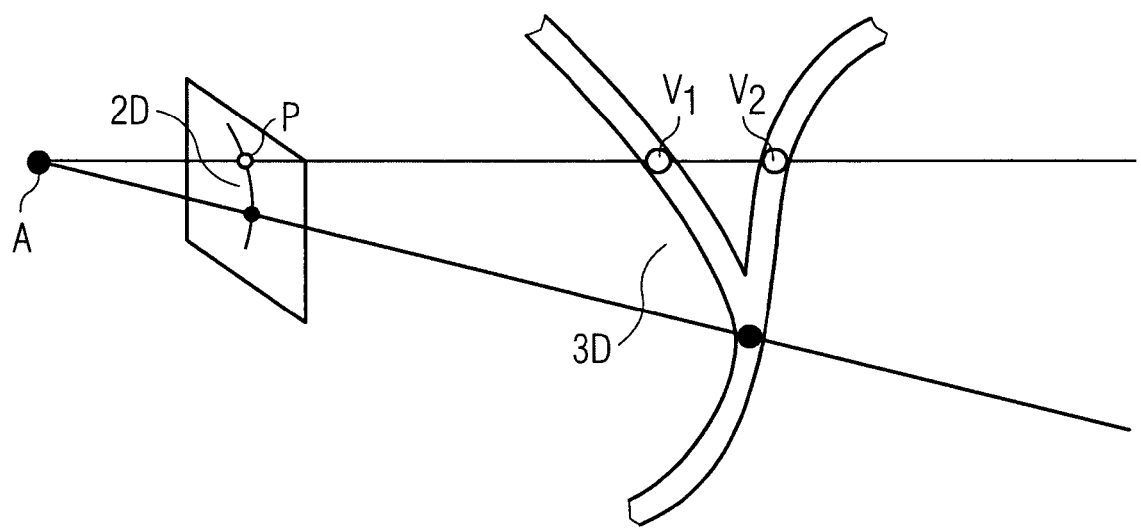
FIG. 1 shows the back projection mentioned at the start from a 2D projection 2D into a 3D volume 3D, with ambiguities occurring.
Figure 2:
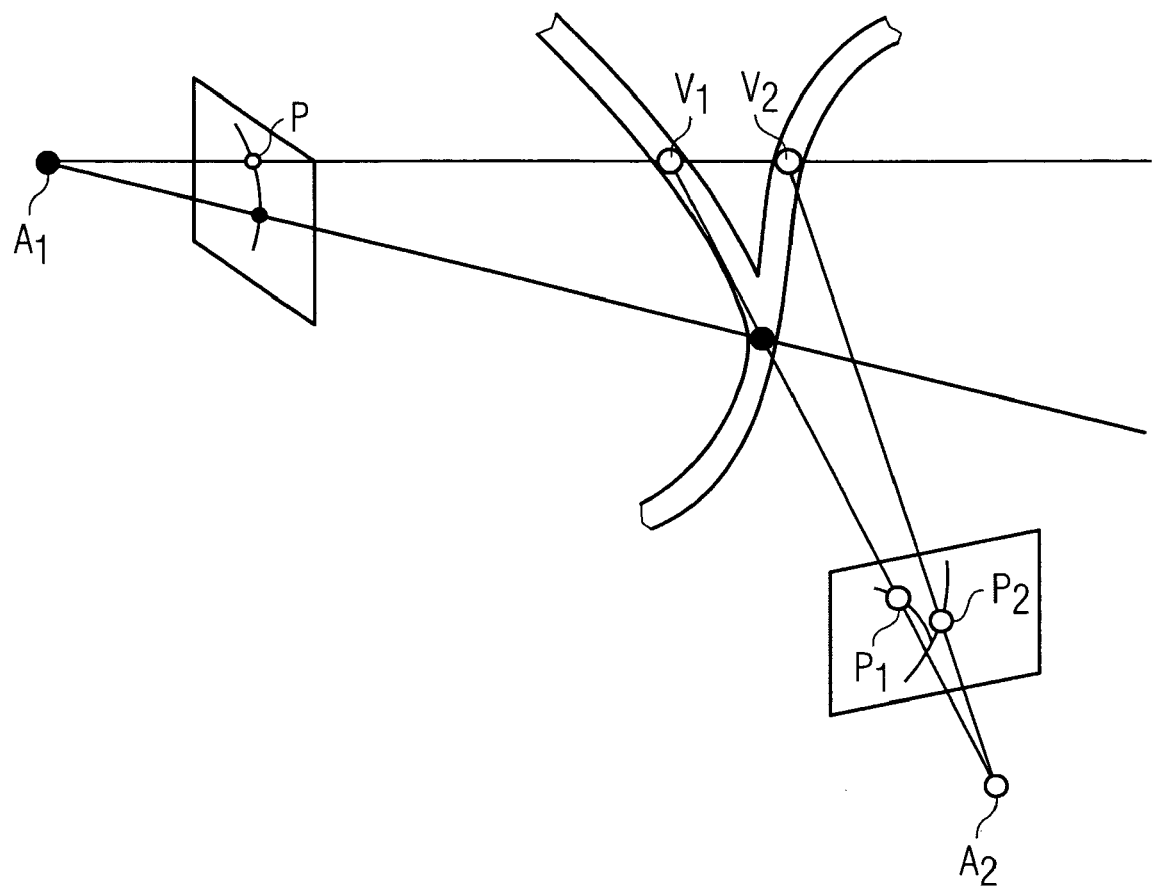
FIG. 2 shows two different views A1 and A2 onto the volume.

FIG. 2 shows two different views A1 and A2 onto the volume. This enables ambiguities to be reduced by selecting a favorable camera position. As regards view A1 it can be seen that the pixel P is able to be mapped or back projected onto the voxels V1 and V2 (ambiguous). As regards view A2 pixels P1 and P2 are able to be mapped or back projected onto voxels V1 and V2 (unambiguous).

A 3D volume tree is provided by 3D rotation angiography. Primarily two problems are resolved:
Prior estimation of the position of the region of interest at a point in time (estimation of the bolus front at point in time t)
Creation of a sequence of optimum positions and orientations for a sequence at points in time, i.e. precisely one optimum imaging view which can be set at a specific point in time.

To approximate the region of interest for which an optimum (imaging) view is to be found, the bolus front is to be estimated as a function of time in the 3D volume. To this end the blood flow is first simulated with the aid of simulation methods, for example from computational fluid dynamics CFD in the individual vessel volume.

To enable an optimum position and alignment sequence to be determined, the term of the optimality and an associated measurement of it is defined which can be compared for different positions.

The measure is dependent on the transformation (position and orientation), under which the volume will be observed. For this purpose the volume is projected perspectively onto the detector plane (that implies the observation of the detector plane as a two-dimensional level in the three-dimensional including a perspective center which in reality corresponds to the x-ray source). In this case a superlinear function is applied to the line integrals along the projection rays and its results are summed. In the exemplary embodiment the line integrals are squared:

$$F(T) = \sum_{i,j} \left( \int_{L_{i,j}} V_T \, dx \right)^2$$

In this case the following applies
T is a transformation of the volume and thus a camera position
$V_T$ is the volume of the vessel under the transformation T
I,j are the indices of the pixels on the detector plane
$L_{I,j}$ is projection ray onto the I,j pixel
Since the measure is to be specifically minimized in the region of interest, it is provided with a weighting mask $\alpha$. The weighting mask ensures that ambiguities in the area of the bolus front are more strongly weighted and thus are not taken into account for the minimization.

$$F(T) = \sum_{i,j} \alpha_{ij}^{t,T} \left( \int_{L_{i,j}} V_T \, dx \right)^2$$

$\alpha^{t,T}$ depends here on the transformation and the time, with the estimation mentioned above being able to be included. The position of the estimated bolus front on the detector plane is only produced by the projection from the simulated blood flow in the 3D volume at a specific point in time.

Assuming the projected center of the bolus front is located on the detector plane at the point $(x_0, y_0)$, then at least one weighting mask can be defined for example by a sum of two-dimensional Gaussian distributions around $(x_0, y_0)$, with variance $\sigma_x^2$ and $\sigma_y^2$, (for simplification with a diagonal covariance matrix of Gaussian distribution). For reasons of clarity an indexing of $\alpha$, $x_k$, $y_k$ $k \in \mathbb{N}_0$ with t,T for identifying the dependency on the time and transformation is omitted below.

$$\alpha(x, y) = \frac{1}{2\pi\sigma_x\sigma_y}\exp\left(-\frac{1}{2}\left(\frac{(x-x_0)^2}{\sigma_x^2} + \frac{(y-y_0)^2}{\sigma_y^2}\right)\right)$$

Starting from the assumption that the bolus front is divided into a number of areas, a single Gaussian distribution does not satisfy the requirements. In this case n subcenters $(x_m, y_m)_{m=1}^n$ are observed for which the weighting shown above is defined. Summation and normalization produce the final weighting mask.

$$\alpha(x, y) = \frac{1}{n}\sum_{m=1}^{n}\alpha_m(x, y)$$
$$= \frac{1}{2n\pi}\sum_{m=1}^{n}\frac{1}{\sigma_{x_m}\sigma_{y_m}}\exp\left(-\frac{1}{2}\left(\frac{(x-x_m)^2}{\sigma_{x_m}^2} + \frac{(y-y_m)^2}{\sigma_{y_m}^2}\right)\right)$$

This time and transformation-dependent transformation mask now makes it possible to define an optimization problem of which the solution is a sequence of transformations $\langle\hat{T}_t\rangle$ of the volume, which make possible the lowest degree of overlaying for each observed point in time t.

$$\langle\hat{T}_t\rangle_{t=0}^{N} = \underset{\langle T_t\rangle_{t=0}^{N}}{\operatorname{argmin}}\left(\sum_t F(T_t)\right)$$

under the auxiliary conditions $$T_t \in U_{T_{t-1}}, \forall t \in \mathbb{N}, t>0$$

with $U_{T_{t-1}}$ describing the set of all possible camera positions or imaging views at point in time t starting from the position $T_{t-1}$ at point in time t−1

$\langle \bullet_j \rangle$ describing a sequence. $(\bullet_0, \bullet_1, \bullet_2, \ldots, \bullet_j)$ To get from the calculated transformation matrix of the volume (calculated with a fixed perspective center and fixed detector plane—corresponds to the reference system detector-source) to an orientation of the x-ray C-arm system, this is converted into a reference system, to which the x-ray C-arm is compatible. In this case, in addition to the possible optimum imaging views, the freedom of movement of the C-arm can be taken into account (at some point there will be a collision with the table or patient). The freedom of movement is restricted without any external influences in today's x-ray systems to an area LAO/RAO of −130° to 130° and CRAN/CAUD to appr. −30° to 30°. The final position sequence is produced taking into account these general conditions.

This can be transferred by a suitable imaging protocol to an x-ray C-arm installation and thus makes possible an angiography sequence with optimum views. This is able to be realized in practice when imaging protocol and installation position are controlled by the 3D application.

Figure 3A:
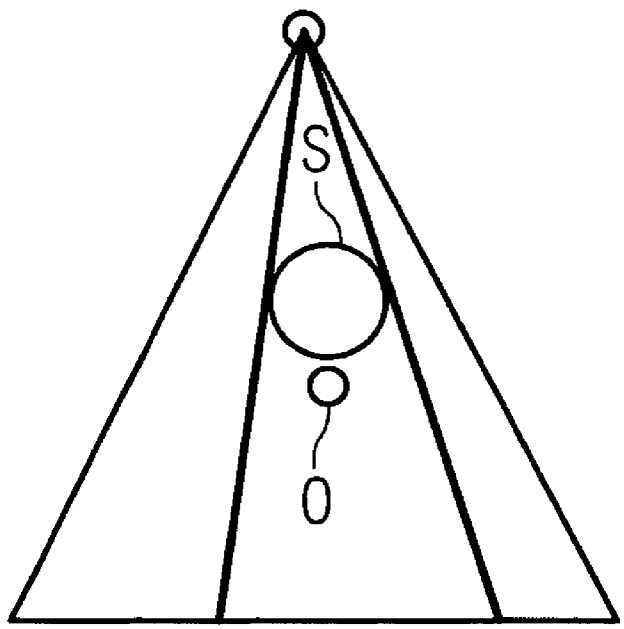
FIGS. 3a and 3b show two different views, in which in one an object O is hidden by an artifact shadow S (FIG. 3a) and in the other the object O is visible next to the artifact shadow S (FIG. 3b).
Figure 3B:
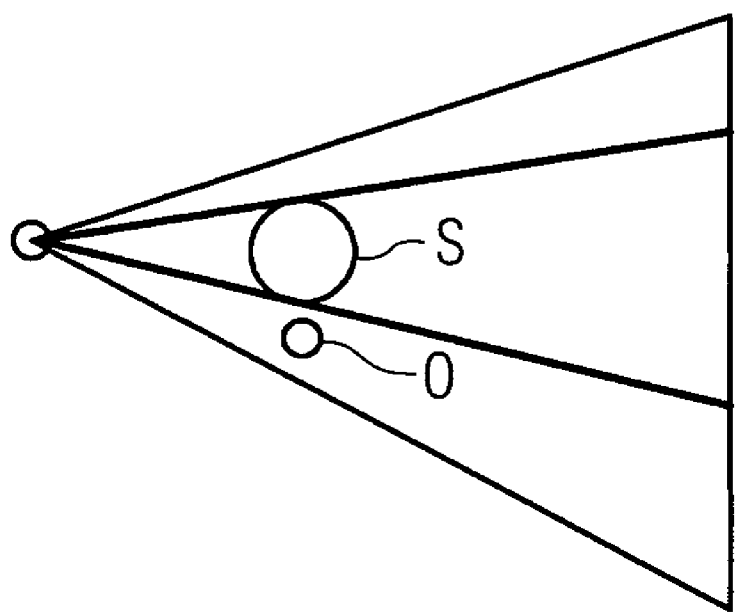

FIGS. 3a and 3b show—as already mentioned above—two different views relating to an object O and a artifact shadow S. If there is an implant causing an artifact in the patient, a changed camera position/view allows a part the otherwise lost information to be obtained. In FIG. 3a the object O lies in the "artifact shadow" of the circle S. In FIG. 3b the object O is visible, since a new position of x-ray source and detector means that it lies "next to" the circle S.

REFERENCES

[1] H. Schmitt, M. Grass, V. Rasche, O. Schramm, S. Haehnel, K. Sartor, An X-Ray-Based Method for the Determination of the Contrast Agent Propagation in 3-D Vessel Structures, IEEE Transactions on Medical Imaging, Vol. 21, No. 3, P. 251-262, March 2002
[2] H. Schmitt, M. Grass, R. Suurmond, T. Köhler, V. Rasche, S. Hähnel, S. Heiland, Reconstruction of blood propagation in three-dimensional rotational X-ray angiography (3D-RA), Computerized Medical Imaging and Graphics, Vol. 29, P. 507-520, 2005
[3] E.-S. Platzer, Visualisierung von Blutfluss im 3-D aus 2-D-Angiogrammen (visualization of blood flow in 3D from 2D angiograms), Thesis, University of Koblenz-Landau and Siemens Medical Solutions Forchheim, August 2006
[4] DE 10 2007 015 306
[5] DE 10 2007 024 451

The invention claimed is:

1. A method for determining an optimum direction of projection for recording with an imaging system a projection image of an object, the method comprising:
   estimating a position, with a computer, of the object at a point in time, wherein the object comprises a fluid front, which flows in a body of a patient; and
   determining an optimum imaging view, with the computer, from which the optimum direction of projection is produced for the estimated position based on a previously determined measurement F(T) of the object, wherein the determined measurement is based on a functional transformation configured to spatially relate a volume of the object to a detector plane of the imaging system, wherein the functional transformation is configured to reduce imaging ambiguities, which can arise when a pixel on the detector plane is mapped onto a voxel of the image of the volume of the object.

2. The method as claimed in claim 1, wherein the steps of the estimating and the determining are repeated.

3. The method as claimed in claim 1, wherein the fluid front comprises a bolus front.

4. The method as claimed in claim 1, wherein the transformation is converted to a coordinate system of the imaging system.

5. The method as claimed in claim 1, wherein the measurement F(T) comprises a superlinear function.

6. The method as claimed in claim 5, wherein the superlinear function comprises a squaring on a line integral applied along a projection ray in the direction of projection.

7. The method as claimed in claim 6, wherein the function is applied along each projection ray and result of the function applied along each projection ray is summed.

8. The method as claimed in claim 1, wherein the measurement F(T) is expressed by a formula:

$$F(T) = \sum_{i,j} f_s \left( \int_{L_{i,j}} V_T \, dx \right),$$

with $f_s$ being a superlinear function,

T being a transformation of a volume of the object and a position with a suitable imaging view, $V_T$ being the volume of the object under the transformation T, I,j being indices of a projection pixel onto a projection plane, and $L_{I,j}$ being a projection ray on which I,j is the projection pixel.

9. The method as claimed in claim 8, wherein the measurement F(T) is weighted by a weighting mask $\alpha$.

10. The method as claimed in claim 9, wherein the measurement F(T) is weighted by the weighting mask a with a formula:

$$F(T) = \sum_{i,j} \alpha_{ij}^{t,T} f_s \left( \int_{L_{i,j}} V_T \, dx \right),$$

with $\alpha^{t,T}$ depending on the transformation T and the point in time t.

11. The method as claimed in claim 10, wherein the previously determined measurement F(T) is the estimated position of the object at the point in time.

12. The method as claimed in claim 11, wherein the weighting mask $\alpha$ is defined by a summation of two-dimensional Gaussian distributions around n projection centers $(x_m, y_m)_{m-1}^n$ of projection pixels on the projection plane with variants $\sigma_{x_m}^2$ and $\sigma_{y_m}^2$ and normalization.

13. The method as claimed in claim 12, wherein the weighting mask $\alpha$ is expressed by a formula:

$$\alpha(x, y) = \frac{1}{n} \sum_{m=1}^{n} \alpha_m(x, y)$$

$$= \frac{1}{2n\pi} \sum_{m=1}^{n} \frac{1}{\sigma_{x_m} \sigma_{y_m}} \exp\left( -\frac{1}{2} \left( \frac{(x - x_m)^2}{\sigma_{x_m}^2} + \frac{(y - y_m)^2}{\sigma_{y_m}^2} \right) \right).$$

14. The method as claimed in claim 13, wherein an indexing $\alpha, x_k, y_k$ $k \in IN_0$ with t,T identifying a dependency of the point in time t and the transformation T is omitted in the formula.

15. The method as claimed in claim 14, wherein a sequence of the transformation to be optimized $\langle \hat{T}_t \rangle$ for a sequence of points in time is expressed by a formula:

$$\langle \hat{T}_t \rangle_{t=0}^N = \operatorname*{argmin}_{\langle T_t \rangle_{t=0}^N} \left( \sum_t F(T_t) \right)$$

under conditions $T_t \in U_{T_{t-1}}, \forall t \in IN, t>0,$ with $U_{T_{t-1}}$ describing a set of all suitable imaging views at the point in time t starting from a position $T_{t-1}$ at a point in time t−1 and $\langle \forall_j \rangle$ describing a sequence $(\bullet_0, \bullet_1, \bullet_2, \ldots, \bullet_j)$.

16. The method as claimed in claim 1, wherein a plurality of measurements are determined at different points in time and are compared with each other for determining a minimum value.

17. The method as claimed in claim 1, wherein an optimum position for recording the projection image is determined.

18. A medical device for examining an object, comprising:
an imaging system that records a projection image of the object in an optimum direction of projection, wherein the object comprises a bolus front, which flows in a body of a patient; and
a computer that is configured to determined the optimum direction of projection, wherein the computer estimates a position of the object at a point in time, and is configured to determined an optimum imaging view from which the optimum direction of projection is produced for the estimated position based on a previously determined measurement F(T) of the object, wherein the determined measurement is based on a functional transformation configured to spatially relate a volume of the object to a detector plane of the imaging system, wherein the functional transformation is configured to reduce imaging ambiguities, which can arise when a pixel on the detector plane is mapped onto a voxel of the image of the volume of the object.

\* \* \* \* \*

UNITED STATES PATENT AND TRADEMARK OFFICE
CERTIFICATE OF CORRECTION

| | | |
|---|---|---|
| PATENT NO. | : 8,244,331 B2 | |
| APPLICATION NO. | : 12/229754 | |
| DATED | : August 14, 2012 | |
| INVENTOR(S) | : Frank Deinzer, Esther-Sabrina Platzer and Matthias Wacker | |

It is certified that error appears in the above-identified patent and that said Letters Patent is hereby corrected as shown below:

Replace term " $(x_m, y_m)_{m-1}^n$ " in claim 12 at column 7 lines 35-36 with -- $(x_m, y_m)_{m=1}^n$ --;

Replace term " $\langle \forall_j \rangle$ " in claim 15 at column 8 line 21 with -- $\langle \bullet_j \rangle$ --.

Signed and Sealed this
Nineteenth Day of February, 2013

Teresa Stanek Rea
*Acting Director of the United States Patent and Trademark Office*